United States Patent
Fujiyoshi et al.

(10) Patent No.: US 9,661,240 B2
(45) Date of Patent: May 23, 2017

(54) RADIATION IMAGING APPARATUS COMPRISING A PIXEL INCLUDING A CONVERSION ELEMENT AND RADIATION IMAGING SYSTEM

(71) Applicant: CANON KABUSHIKI KAISHA, Tokyo (JP)

(72) Inventors: Kentaro Fujiyoshi, Tokyo (JP); Minoru Watanabe, Honjo (JP); Keigo Yokoyama, Honjo (JP); Masato Ofuji, Takasaki (JP); Jun Kawanabe, Kumagaya (JP); Hiroshi Wayama, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/696,936

(22) Filed: Apr. 27, 2015

(65) Prior Publication Data

US 2015/0316664 A1 Nov. 5, 2015

(30) Foreign Application Priority Data

May 1, 2014 (JP) ................................ 2014-094876

(51) Int. Cl.
*H05G 1/64* (2006.01)
*H04N 5/32* (2006.01)
*G01T 1/24* (2006.01)
*G01N 23/04* (2006.01)
*G01T 1/20* (2006.01)

(52) U.S. Cl.
CPC ............... *H04N 5/32* (2013.01); *G01N 23/04* (2013.01); *G01T 1/2018* (2013.01); *G01T 1/247* (2013.01)

(58) Field of Classification Search
CPC .......... A61B 6/00; A61B 6/025; A61B 6/035; A61B 6/42; A61B 6/4208; A61B 6/4216; A61B 6/4241; G01T 1/00; G01T 1/003; G01T 1/10; G01T 1/16; G01T 1/20; G01T 1/2004; G01T 1/2006
USPC ..... 378/98.8, 98.9, 98.11, 98.12, 98.4, 98.6; 250/370.01, 370.04, 370.07, 370.08, 250/370.09
See application file for complete search history.

(56) References Cited

U.S. PATENT DOCUMENTS 7,470,908 B2   12/2008 Ishii et al. ............... 250/370.08
7,573,038 B2    8/2009 Yokoyama et al. ..... 250/370.09
(Continued)

FOREIGN PATENT DOCUMENTS

JP      A 2011-255020      12/2011
WO     WO 2011/135917 A    11/2011

*Primary Examiner* — Jason McCormack
(74) *Attorney, Agent, or Firm* — Fitzpatrick, Cella, Harper & Scinto

(57) ABSTRACT

A pixel includes a conversion element detecting radiation, and a switch between the element and a signal line. A readout unit reads out a signal on the signal line. The readout unit includes a reset unit that resets a potential of the signal line. A period during which the readout unit reads out a signal on the signal line includes a first period during which the signal line is reset, and a signal on the signal line in a state that the switch is not turned on is read out, and a second period during which the signal line is reset, and a signal on the signal line due to the switch being turned on is read out. The processing unit calculates a difference between the signals read out in the second and first periods.

13 Claims, 15 Drawing Sheets

(56) References Cited

U.S. PATENT DOCUMENTS

| | | | |
|---|---|---|---|
| 7,718,973 B2 | 5/2010 | Endo et al. | 250/370.08 |
| 7,724,874 B2 | 5/2010 | Kameshima et al. | 378/98.12 |
| 7,732,776 B2 | 6/2010 | Takenaka et al. | 250/369 |
| 7,732,778 B2 | 6/2010 | Yokoyama et al. | 250/370.08 |
| 7,839,977 B2 | 11/2010 | Kameshima et al. | 378/116 |
| 7,897,930 B2 | 3/2011 | Mochizuki et al. | 250/370.09 |
| 8,072,514 B2 | 12/2011 | Takenaka et al. | 348/246 |
| 8,107,588 B2 | 1/2012 | Kameshima et al. | 378/62 |
| 8,247,779 B2 | 8/2012 | Kameshima et al. | 250/370.09 |
| 8,680,472 B2 | 3/2014 | Mochizuki et al. | 250/370.09 |
| 8,723,996 B2 | 5/2014 | Yokoyama et al. | 348/294 |
| 2004/0156473 A1* | 8/2004 | Nonaka | H05G 1/26 378/62 |
| 2010/0086102 A1* | 4/2010 | Kameshima | G01T 1/00 378/62 |
| 2011/0305321 A1 | 12/2011 | Iwakiri et al. | 378/98.8 |
| 2012/0018640 A1* | 1/2012 | Shimizukawa | G01T 1/16 250/354.1 |
| 2013/0032696 A1 | 2/2013 | Tajima | 250/208.1 |

\* cited by examiner

F I G. 9
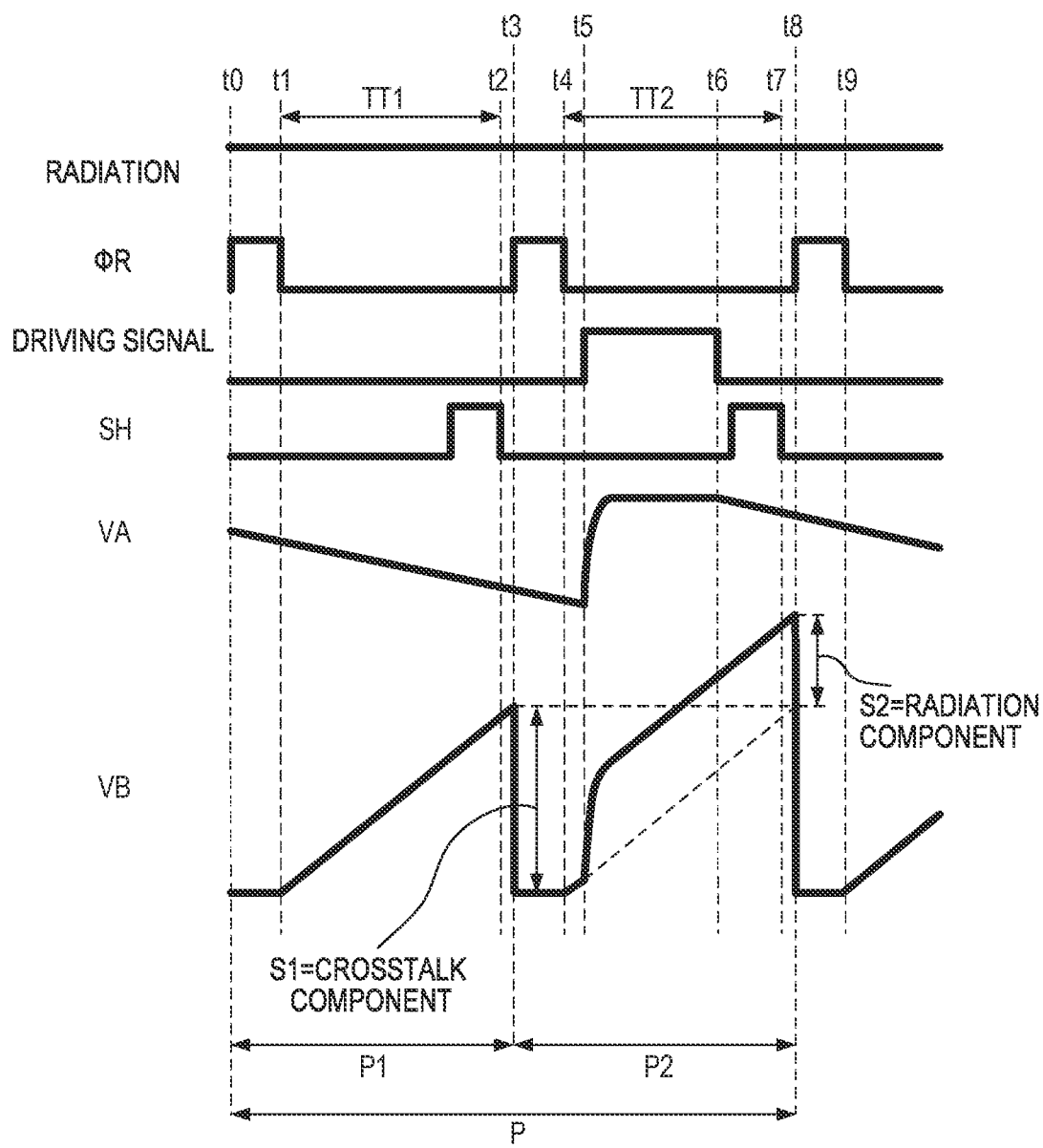

RADIATION IMAGING APPARATUS COMPRISING A PIXEL INCLUDING A CONVERSION ELEMENT AND RADIATION IMAGING SYSTEM

BACKGROUND OF THE INVENTION

Field of the Invention

The present invention relates to a radiation imaging apparatus and a radiation imaging system.

Description of the Related Art

Radiation imaging apparatuses having arrays of pixels in which switches such as TFTs (thin film transistors) and conversion elements such as photoelectric conversion elements are combined have been put to practical use as radiation imaging apparatuses used for medical imaging diagnosis and non-destructive examination by means of radiation such as X-rays. Each switch is arranged between a conversion element and a column signal line, and by turning on a switch, a signal is read out from the conversion element via the column signal line.

Japanese Patent Laid-Open No. 2011-255020 discloses a radiation detection apparatus having a correlated double sampling unit (CDS unit). The CDS unit includes a first sample holding circuit, a second sample holding circuit, and a differential amplifier. The first sample holding circuit holds a sample of a remnant component (noise component) of a signal charge, and the second sample holding circuit holds a sample of a signal charge (noise component+signal component). The differential amplifier amplifies the difference between the output of the first sample holding circuit and the output of the second sample holding circuit.

Parasitic capacitances are formed between a column signal line for reading out signals from conversion elements and the electrodes of the multiple conversion elements in the column in which the column signal line is arranged. The column signal line and the conversion elements are capacitively coupled due to these parasitic capacitances, and thus crosstalk can occur. For this reason, when the signals are read out via the column signal lines from the conversion elements of pixels in a row, if the potential of the electrodes of the conversion elements of pixels in another row changes due to photoelectric conversion, the potential of the column signal lines can change due to crosstalk. This can cause the SN ratio of the readout signals to decrease.

Note that correlated double sampling (CDS) is a technique for canceling KTC noise, which is based on the premise that the noise component in the first instance of sampling is the same as the noise component in the second instance of sampling. Note that with usual CDS, the first instance of sampling is performed after a reset operation for the potential of the column signal line or the conversion element, and thereafter, the second instance of sampling is performed without the reset operation being performed once again. If the reset operation is performed between the first instance of sampling and the second instance of sampling, the noise component (KTC noise) sampled in the first instance of sampling will be different from the noise component (KTC noise) sampled in the second instance of sampling. Accordingly, in this case, the noise component cannot be canceled.

SUMMARY OF THE INVENTION

The present invention provides a technique that is advantageous for reducing the influence of crosstalk.

A first aspect of the present invention provides a radiation imaging apparatus, comprising: a pixel including a conversion element configured to convert radiation into an electric signal, and a switch configured to connect the conversion element to a signal line; a readout unit configured to read out a signal that appears in the signal line; and a signal processing unit, wherein the readout unit includes a reset unit configured to reset a potential of the signal line, a period during which the readout unit reads out a signal that appears in the signal line includes: a first period including an operation in which the potential of the signal line is reset by the reset unit, and thereafter, an operation in which a signal that appears in the signal line in a state in which the switch is not turned on is read out, and a second period including an operation in which the potential of the signal line is reset by the reset unit, and thereafter, an operation in which a signal that appears in the signal line due to the switch being turned on is read out, and the signal processing unit calculates a difference between the signal read out by the readout unit in the second period and the signal read out by the readout unit in the first period.

Further features of the present invention will become apparent from the following description of exemplary embodiments with reference to the attached drawings.

BRIEF DESCRIPTION OF THE DRAWINGS

FIG. 9 is a diagram showing operations performed by the radiation imaging apparatus according to the first embodiment of the present invention.

DESCRIPTION OF THE EMBODIMENTS

Hereinafter, the present invention will be described via exemplary embodiments thereof, with reference to the accompanying drawings.

Figure 1:
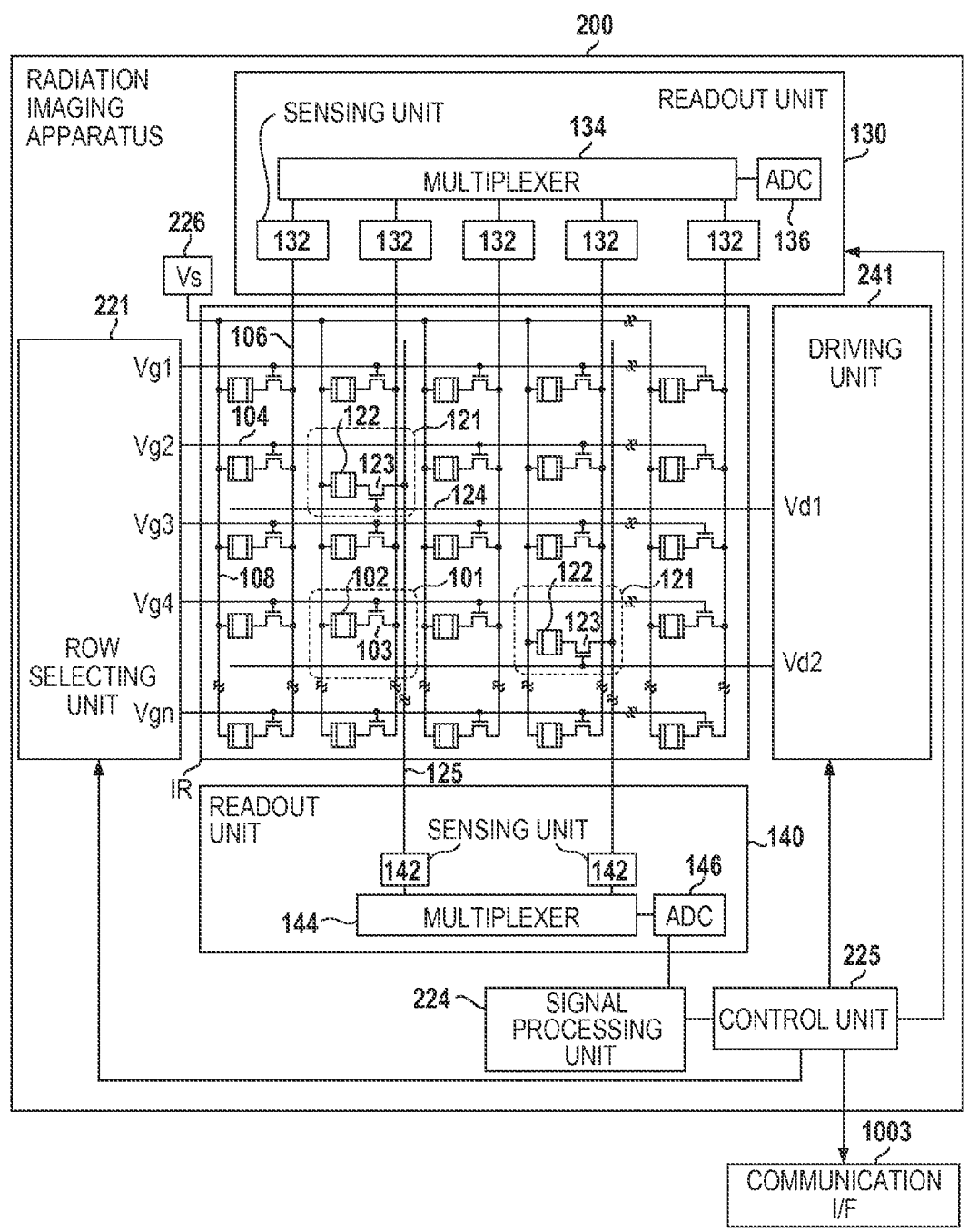
FIG. 1 is a diagram showing a configuration of a radiation imaging apparatus according to a first embodiment of the present invention.

FIG. 1 shows a configuration of a radiation imaging apparatus 200 according to a first embodiment of the present invention. The radiation imaging apparatus 200 has multiple pixels that are arrayed in an imaging area IR so as to form multiple rows and multiple columns. The multiple pixels include multiple imaging pixels 101 for obtaining a radiation image, and a sensing pixel 121 for monitoring the irradiation of radiation. The imaging pixels 101 each include a first conversion element 102 that converts radiation into an electric signal, and a first switch 103 that is arranged between a column signal line 106 and the first conversion element 102. The sensing pixels 121 each include a second conversion element 122 that converts radiation into an electric signal, and a second switch 123 that is arranged between a sensing signal line 125 and the second conversion element 122. The sensing pixel 121 can be arranged in the same column as a portion of the multiple imaging pixels 101.

The first conversion element 102 and the second conversion element 122 can be formed using a scintillator that converts radiation into light and a photoelectric conversion element that converts the light into an electric signal. The scintillator can usually be formed in a sheet shape so as to cover the imaging area IR, and it can be shared by multiple pixels. Alternatively, the first conversion element 102 and the second conversion element 122 can be formed using conversion elements that convert radiation directly into light.

The first switch 103 and the second switch 123 can, for example, include a thin film transistor (TFT) in which an active area is formed by a semiconductor such as amorphous silicon or polycrystalline silicon (preferably polycrystalline silicon).

The radiation imaging apparatus 200 has multiple column signal lines 106 and multiple driving lines 104. A column signal line 106 corresponds to one of the multiple columns in the imaging area IR. A driving line 104 corresponds to one of the multiple rows in the imaging area IR. The driving lines 104 are driven by a row selecting unit 221.

A first electrode of the first conversion element 102 is connected to a first main electrode of the first switch 103, and a second electrode of the first conversion element 102 is connected to a bias line 108. Here, one bias line 108 extends in the column direction and is connected in common to the second electrodes of multiple conversion elements 102 aligned in the column direction. The bias line 108 receives a bias voltage Vs from a power supply circuit 226. The second main electrodes of the first switches 103 of multiple imaging pixels 101 that form one column are connected to one column signal line 106. The control electrodes of the first switches 103 of multiple imaging pixels 101 that form one row are connected to one driving line 104.

The multiple column signal lines 106 are connected to a readout unit 130. Here, the readout unit 130 can include multiple sensing units 132, a multiplexer 134, and an analog-digital converter (referred to below as "AD converter") 136. Each of the column signal lines 106 is connected to a corresponding sensing unit 132 among the multiple sensing units 132 of the readout unit 130. Here, one column signal line 106 corresponds to one sensing unit 132. A sensing unit 132 includes a differential amplifier, for example. The multiplexer 134 selects the multiple sensing units 132 in a predetermined order and supplies the signal from a selected sensing unit 132 to the AD converter 136. The AD converter 136 converts the supplied signal into a digital signal and outputs it.

A first electrode of the second conversion element 122 is connected to a first main electrode of the second switch 123, and a second electrode of the second conversion element 122 is connected to a bias line 108. The second main electrode of the second switch 123 is connected to the sensing signal line 125. The control electrode of the second switch 123 is electrically connected to the driving line 124. The radiation imaging apparatus 200 can have multiple sensing signal lines 125. One or more sensing pixels 121 can be connected to one sensing signal line 125. The driving line 124 is driven by the driving unit 241. One or more sensing pixels 121 can be connected to one driving line 124.

The sensing signal lines 125 are connected to the readout unit 140. Here, the readout unit 140 can include multiple sensing units 142, a multiplexer 144, and an AD converter 146. Each of the sensing signal lines 125 can be connected to a corresponding sensing unit 142 among the multiple sensing units 142 of the readout unit 140. Here, one sensing signal line 125 corresponds to one sensing unit 142. A sensing unit 142 includes a differential amplifier, for example. The multiplexer 144 selects the multiple sensing units 142 in a predetermined order and supplies the signal from a selected sensing unit 142 to the AD converter 146. The AD converter 146 converts the supplied signal into a digital signal and outputs it.

The output of the readout unit 140 (AD converter 146) is supplied to a signal processing unit 224 and is processed by the signal processing unit 224. Based on the output of the readout unit 140 (AD converter 146), the signal processing unit 224 outputs information indicating irradiation of radiation on the radiation imaging apparatus 200. Specifically, the signal processing unit 224 senses irradiation of radiation on the radiation imaging apparatus 200 and calculates the irradiation amount and/or the integrated irradiation amount of the radiation, for example. The control unit 225 controls the row selecting unit 221, the driving unit 241, and the readout unit 130 based on the information from the signal processing unit 224. For example, based on the information from the signal processing unit 224, the control unit 225 controls the start and end of exposure (accumulation of charges corresponding to the emitted radiation in the imaging pixels 101). The signal processing unit 224 and the control unit 225 can be implemented by, for example, an application specific integrated circuit (ASIC)), or a computer that reads out and executes computer executable instructions (programs) recorded on a storage medium.

Figure 2:
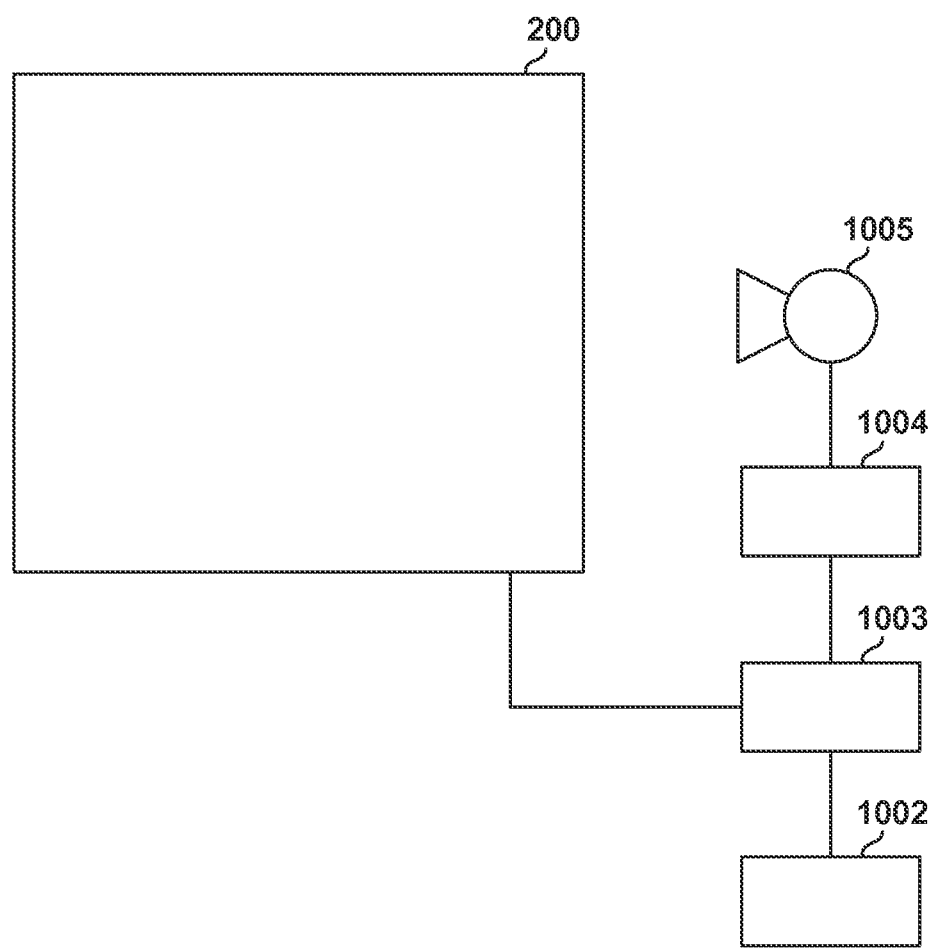
FIG. 2 is a diagram showing an example of a configuration of a radiation imaging system that includes the radiation imaging apparatus.

A configuration of a radiation imaging system including the radiation imaging apparatus 200 is illustrated in FIG. 2. In addition to the radiation imaging apparatus 200, the radiation imaging system includes a controller 1002, an interface 1003, a radiation source interface 1004, and a radiation source 1005.

The controller 1002 can receive input of radiation dose A, an irradiation time B (ms), a tube current C (mA), a tube voltage D (kV), and a radiation sensing area (ROI), which is an area in which radiation is to be monitored, and the like.

If an exposure switch attached to the radiation source 1005 is operated, radiation is radiated from the radiation source 1005. When the integrated value of the signals read out from the sensing pixels 121 arranged in the radiation sensing area (ROI) reaches a radiation dose A', for example, the control unit 225 of the radiation imaging apparatus 200 sends an exposure stop signal to the radiation source interface 1004 via the interface 1003. In response to this, the radiation source interface 1004 causes the radiation source 1005 to stop radiating radiation. Here, the radiation dose A' can be determined by the control unit 225 based on the radiation dose A, the radiation irradiation intensity, communication delay between units, processing delay, and the like. When the time for emitting radiation reaches an irradiation time B, the radiation source 1005 stops the emission of radiation regardless of whether or not there is an exposure stop signal.

In the first embodiment, image information for locations at which the sensing pixels 121 exist cannot be read out, but image information for the locations at which the sensing pixels 121 exist can be obtained by performing interpolation processing using the output of the imaging pixels 101 in the periphery of the sensing pixels 121.

Figure 3:
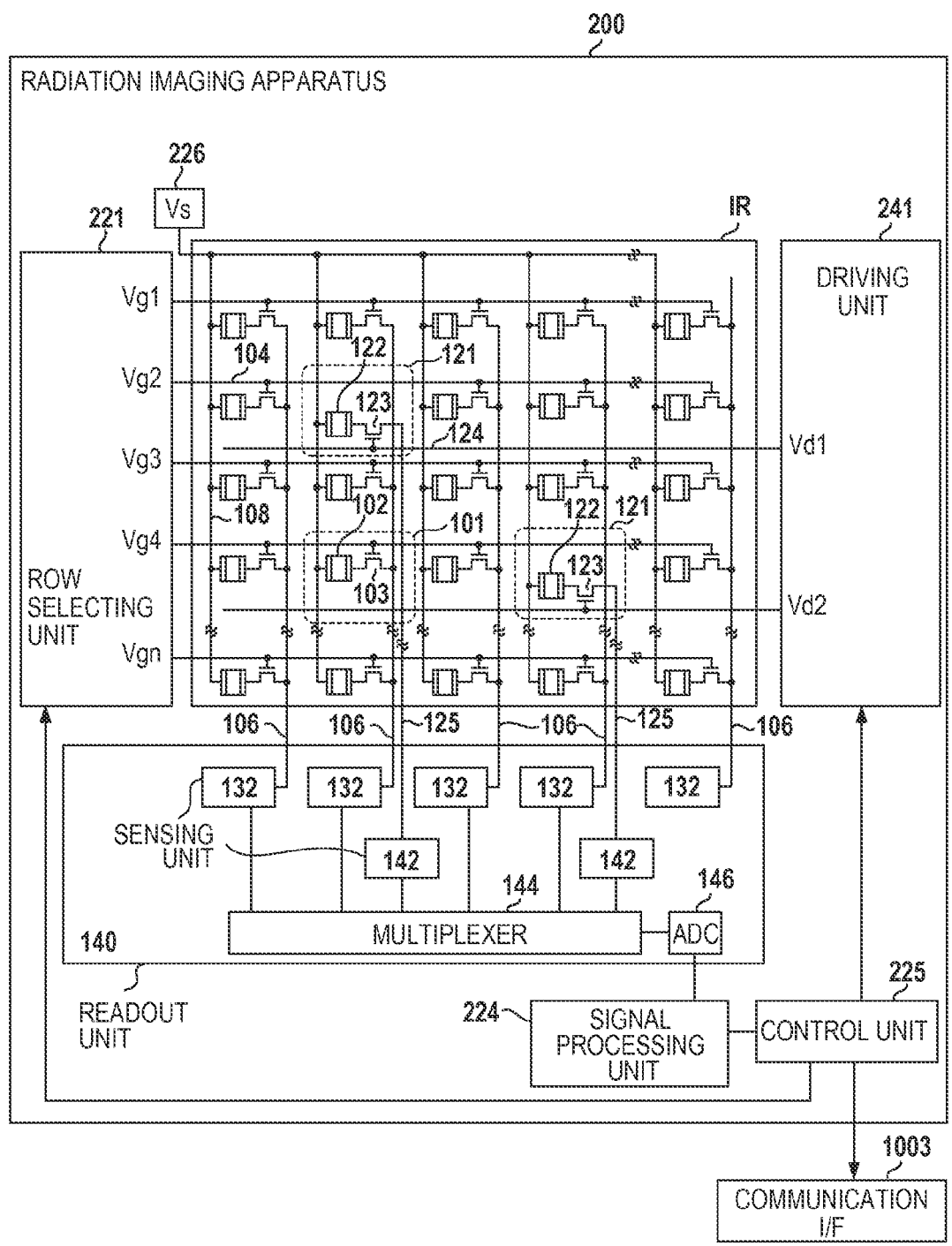
FIG. 3 is a diagram showing a configuration of a modified example of the radiation imaging apparatus according to the first embodiment of the present invention.

In the configuration example shown in FIG. 1, the signals from the imaging pixels 101 and the signals from the sensing pixels 121 are read out by separate readout units 130 and 140, but as illustrated in FIG. 3, they may be read out by a common readout unit 140.

Figure 4:
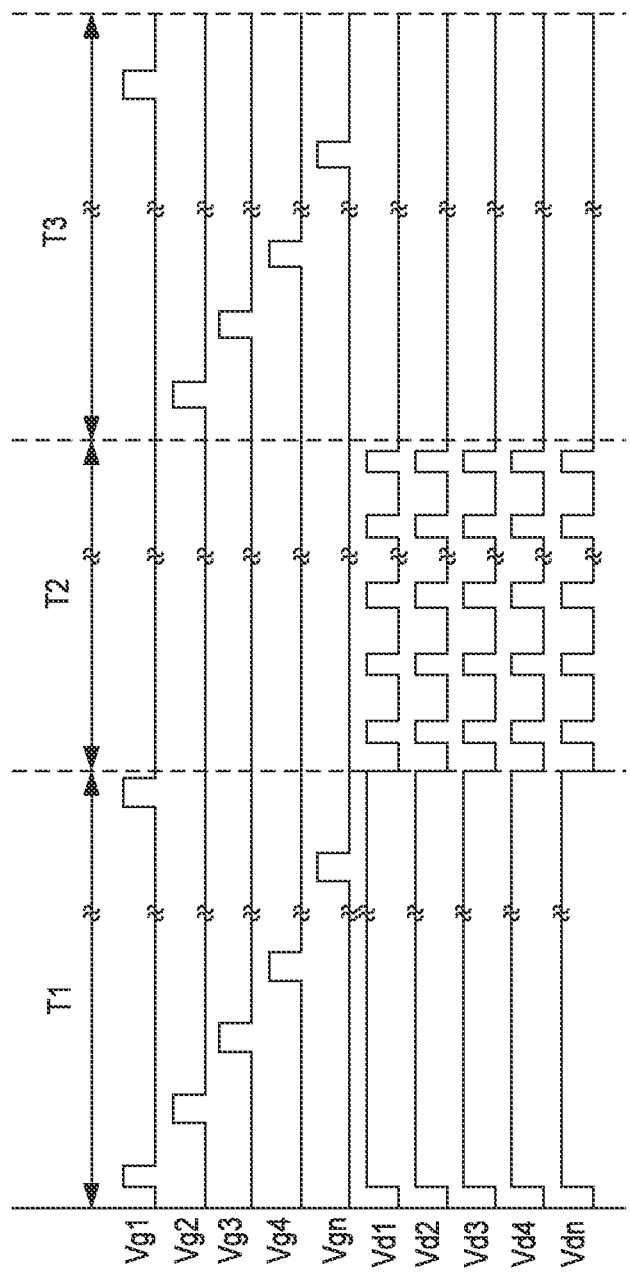
FIG. 4 is a diagram showing operations performed by the radiation imaging apparatus according to the first embodiment of the present invention.

FIG. 4 illustrates operations of the radiation imaging apparatus 200 according to the first embodiment of the present invention. In the description below, let Vg1 to Vgn be signals that are applied to the driving line 104 that drives the imaging pixels 101, and let Vd1 to Vdn be signals that are applied to the driving line 124 that drives the sensing pixels 121. The first switch 103 and the second switch 123 turn on when the signal supplied to the gate is at a high level, and turn off when the signal supplied to the gate is at a low level.

Period T1 is a period of waiting for the start of irradiation of radiation. Specifically, period T1 is from when the power supply of the radiation imaging apparatus 200 is switched on and a radiation image can be captured, until when the exposure switch of the radiation source 1005 is operated and the irradiation of radiation is sensed.

In period T1, Vd1 to Vdn are fixed at the high level, and the second switches 123 of the sensing pixels 121 are fixed in the on state. The signal read out by the readout unit 140 from the sensing pixel 121 is processed by the signal processing unit 224, and thus the start of irradiation of radiation is sensed. When the start of irradiation of radiation is sensed, period T2 is entered. In period T1, in order to remove dark currents generated in the conversion elements 102, it is desirable that the first conversion elements 102 are periodically reset to a fixed potential. In this example, the voltages Vg1 to Vgn of the driving lines 104 are switched to the high level in sequence, and the conversion elements 102 are electrically connected to the column signal lines 106, which are fixed at a constant voltage. This prevents charges resulting from the dark currents from being accumulated over a long time in the conversion elements 102. The length of period T1 varies significantly depending on the shooting method, shooting conditions, and the like, and for example, can be several seconds to several minutes.

Period T2 is a period during which radiation is emitted. For example, period T2 is a period from when the start of irradiation of radiation is sensed to when the exposure amount of the radiation reaches an optimal radiation dose. It can also be said that period T2 is a period during which the irradiation amount of radiation is monitored. In period T2, Vd1 to Vdn are intermittently switched to the high level, and the second switches 123 of the sensing pixels 121 are intermittently switched to the on state.

The signals read out by the readout unit 140 from the sensing pixels 121 are processed by the signal processing unit 224, and thus the radiation dose is sensed. In period T2, the signals Vg1 to Vgn that are applied to the driving lines 104 are switched to the low level. Accordingly, the generated charges are accumulated in the first conversion elements 102 of the imaging pixels 101. The length of period T2 varies significantly depending on the shooting method, shooting conditions, and the like, and for example, can be around one millisecond to around several hundred milliseconds.

When the integrated value of the signals read out from the sensing pixels 121 arranged in the radiation sensing area (ROI) reaches the radiation dose A', the control unit 225 causes the operation of the radiation imaging apparatus 200 to enter period T3. Also, at this time, the control unit 225 sends the exposure stop signal to the radiation source interface 1004 via the interface 1003.

Period T3 is a period during which signals accumulated in the imaging pixels 101 due to the radiation are read out after the irradiation of radiation has ended. In period T3, Vd1 to Vdn are switched to the low level. In period T3, in order to prevent the sensing signal line 125 from floating, it is preferable that the sensing signal line 125 is connected to a fixed potential.

In period T3, Vg1 to Vgn are switched to the high level in sequence in order to scan multiple rows. The signals accumulated in the imaging pixels 101 are read out by the readout unit 140. In this example, the row to which the high level is first applied is determined according to the row to which the high level was last applied in period T1, such that the accumulation times for the imaging pixels 101 are the same. In FIG. 4, the row to which the high level was last applied in period T1 is the row corresponding to Vg1, and therefore in period T3, the high level is applied in sequence starting from the row corresponding to Vg2.

In the first embodiment, the second conversion elements 122, which are conversion elements of the sensing pixels 121, are connected to the sensing signal lines 125, which are signal lines provided separately from the column signal lines 106 for reading out the signals from the imaging pixels 101, and therefore the imaging pixels 101 are not connected to the sensing signal lines 125. Accordingly, it is possible to reduce the parasitic capacitances of the sensing signal lines 125, making it possible to monitor the irradiation of radiation with a high responsiveness.

Also, in the first embodiment, by providing the second switches 123, which are switches for the sensing pixels 121, the number of sensing signal lines 125 can be reduced and irradiation of radiation can be sensed by each of the sensing pixels 121. Here, a configuration in which radiation can be sensed by each of the sensing pixels 121, or in each radiation sensing area (ROI) that includes at least one sensing pixel 121, contributes to the realization of more suitable radiation dose control and exposure control.

Figure 5:
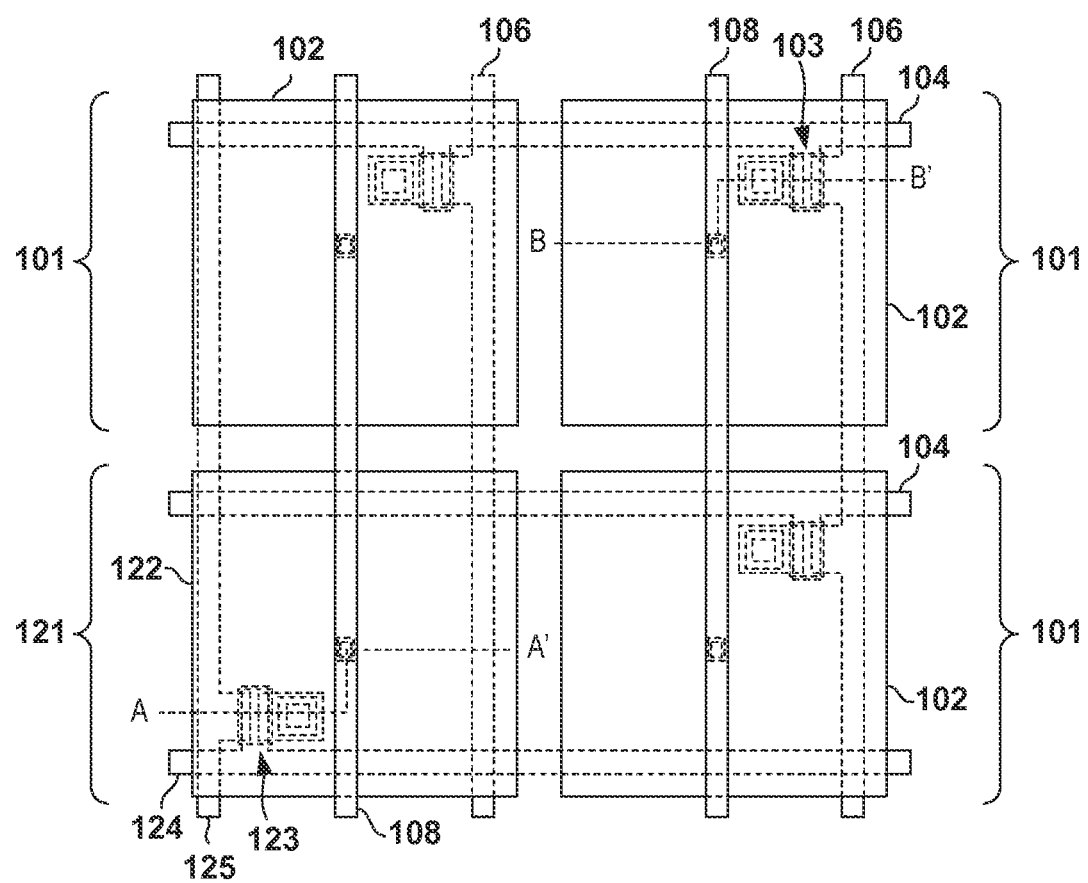
FIG. 5 is a plan view showing a configuration of imaging pixels and a sensing pixel in the radiation imaging apparatus according to the first embodiment of the present invention.
Figure 6A:
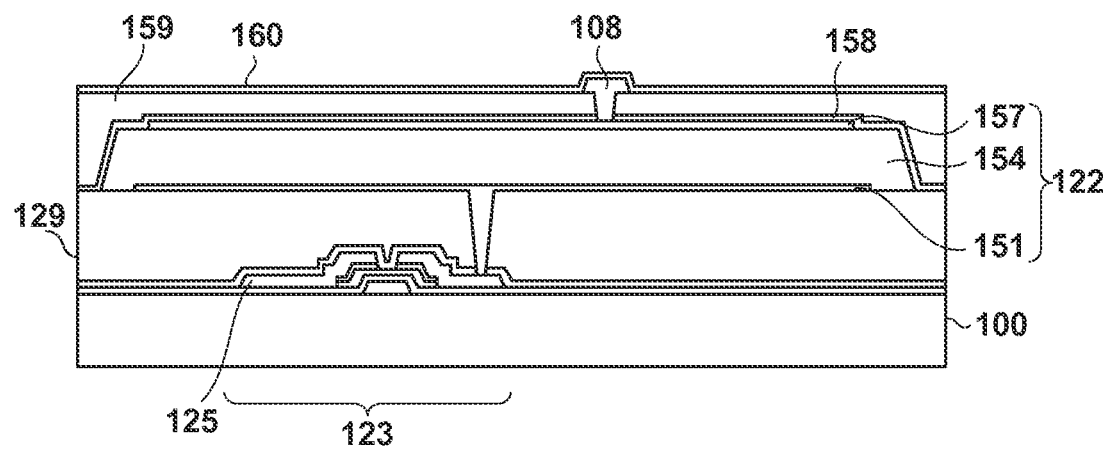
FIG. 6A is a cross-sectional view taken along line A-A' in FIG. 5.

FIG. 5 is a plan view showing a configuration of imaging pixels 101 and a sensing pixel 121 in the radiation imaging apparatus 200 according to the first embodiment of the present invention. Here, the plan view is equivalent to an orthographic projection on a surface parallel to the imaging area IR of the radiation imaging apparatus 200. FIG. 6A is a cross-sectional view taken along line A-A' in FIG. 5, and FIG. 6B is a cross-sectional view taken along line B-B' in FIG. 5.

As illustrated in FIG. 5 and FIG. 6A, the sensing pixel 121 includes the second conversion element 122 and the second switch 123. In this example, radiation is converted into light by a scintillator (not shown), and the second conversion element 122 converts the light into a charge and accumulates it. Note that the second conversion element 122 may be configured to convert the radiation directly into a charge. The second switch 123 includes a TFT (thin film transistor) that outputs an electric signal corresponding to the charge accumulated in the second conversion element 122. The second conversion element 122 can be a PIN photodiode 154, for example. The second conversion element 122 is connected to the sensing signal line 125 via the second switch 123. The second conversion element 122 can be arranged above the second switch 123 arranged on the insulating support substrate 100, which is a glass substrate or the like, with an interlayer insulating layer 129 interposed therebetween. For example, the second conversion element 122 can be configured by the first electrode 151, the PIN photodiode 154, and the second electrode 157.

Above the second conversion element 122, a protective film 158, a second interlayer insulating layer 159, a bias line 108, and a protective film 160 are arranged in the stated order. A flattening film and a scintillator (not shown) are arranged above the protective film 160. The second electrode 157 is connected to the bias line 108 via a contact hole. ITO, which has a light-transmitting property, is used for the second electrode 157, which is configured to be able to transmit light after it has been converted from radiation by the scintillator (not shown).

Figure 6B:
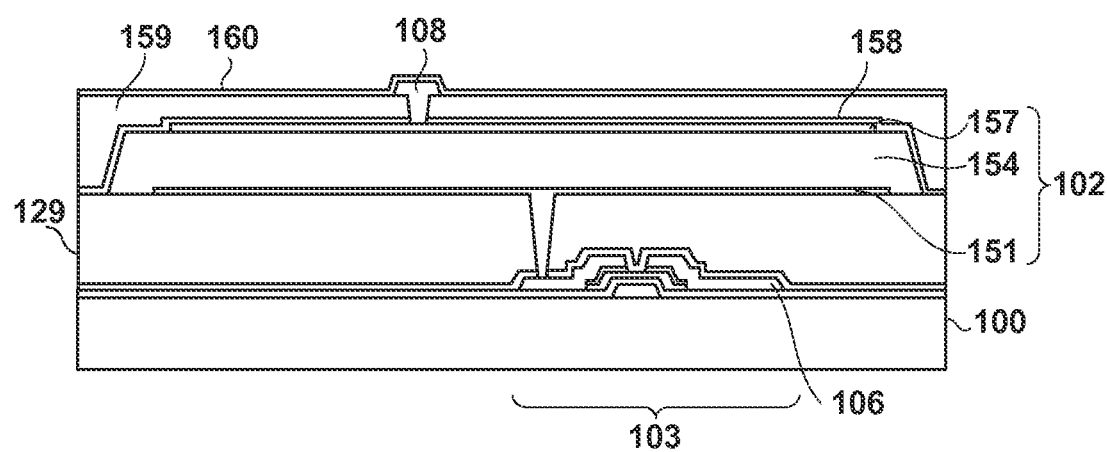
FIG. 6B is a cross-sectional view taken along line B-B' in FIG. 5.

As illustrated in FIG. 5 and FIG. 6B, the imaging pixel 101 includes the first conversion element 102 and the first switch 103. In this example, radiation is converted into light by a scintillator (not shown), and similarly to the second conversion element 122, the first conversion element 102 converts the light into a charge and accumulates it. Note that the first conversion element 102 may be configured to convert the radiation directly into a charge. The first switch 103 includes a TFT (thin film transistor) that outputs an electric signal corresponding to the charge accumulated in the first conversion element 102. The first conversion element 102 can be the PIN photodiode 154, for example. The first conversion element 102 is connected to the column signal line 106 via the first switch 103. The first conversion element 102 can be arranged above the first switch 103 arranged on the insulating support substrate 100, which is a glass substrate or the like, with an interlayer insulating layer 129 interposed therebetween. For example, the first conversion element 102 can be configured by the first electrode 151, the PIN photodiode 154, and the second electrode 157. The first conversion element 102 and the second conversion element 122 may be configured by a MIS sensor for example.

Figure 7:
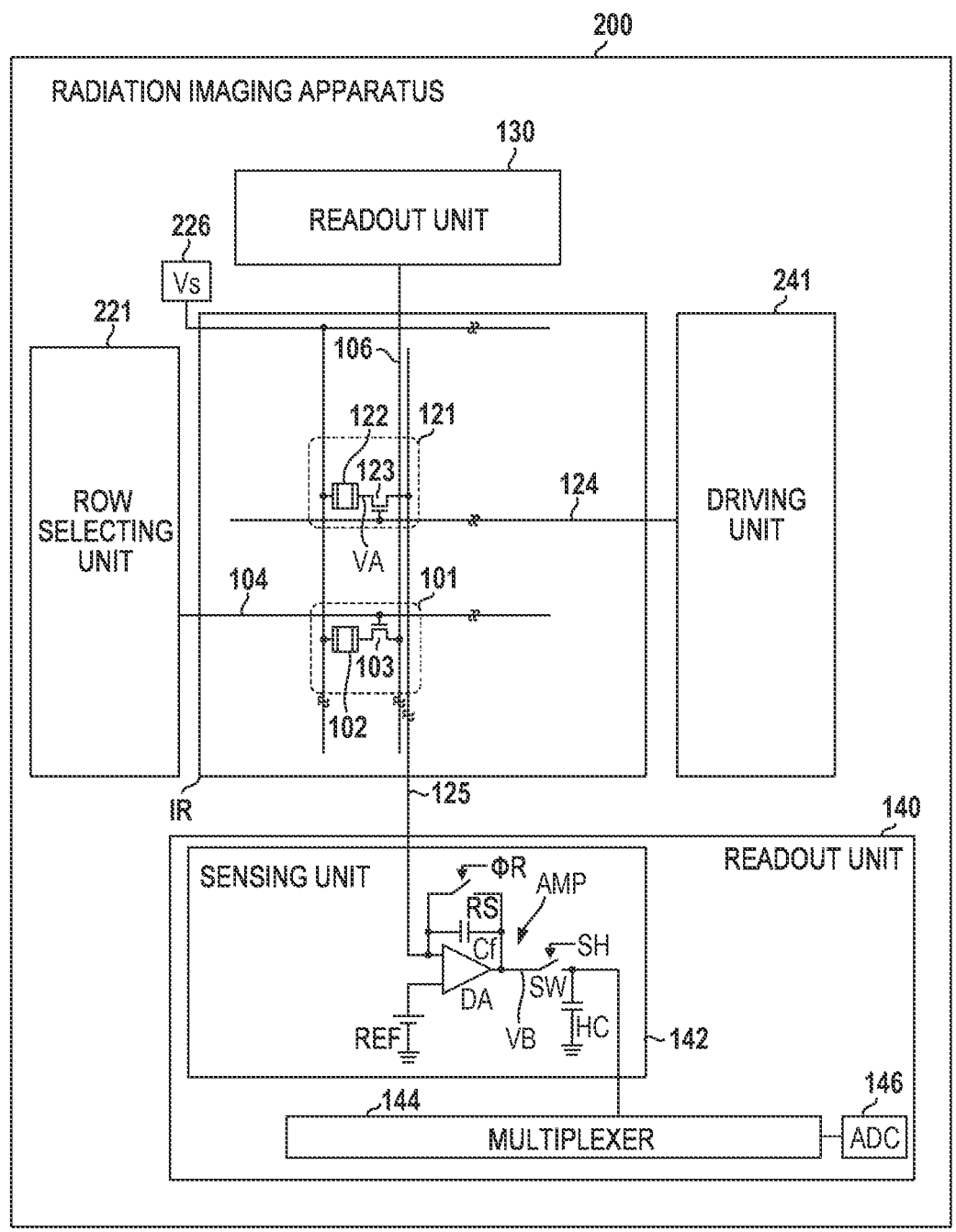
FIG. 7 is a diagram showing a configuration of the radiation imaging apparatus according to the first embodiment of the present invention.
Figure 8:
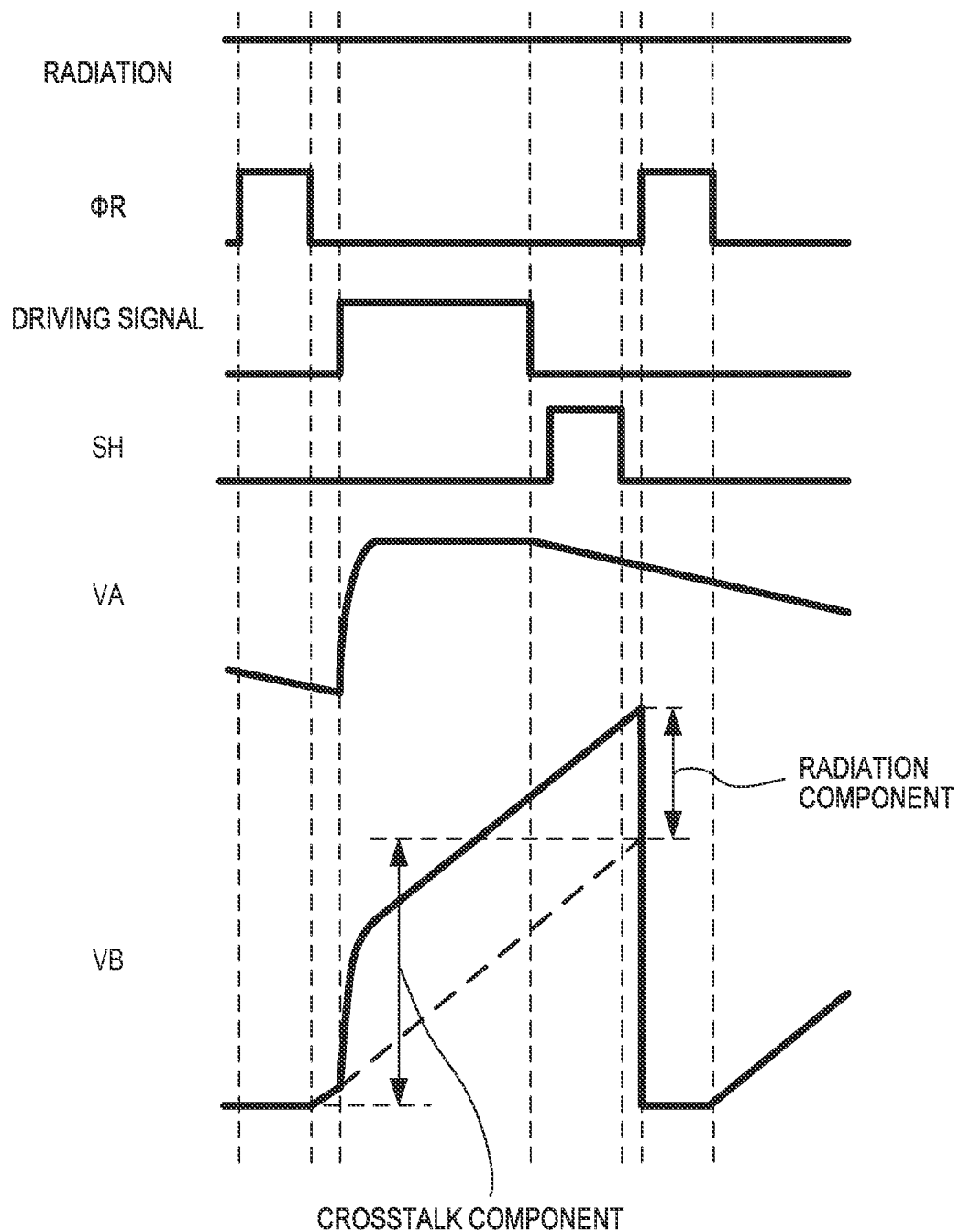
FIG. 8 is a diagram showing a comparative example.

A specific example of the configuration and operations of the readout unit 140 will be provided next with reference to FIGS. 7 to 9. FIG. 7 shows an example of a configuration of the readout unit 140. FIG. 8 shows a comparative example. FIG. 9 shows an example of operations performed by the readout unit 140.

The sensing unit 142 of the readout unit 140 includes an amplification circuit AMP, a holding capacitor HC, and a sampling switch SW. The amplification circuit AMP includes a differential amplifier DA that has a first input terminal, a second input terminal, and an output terminal, and a feedback capacitor Cf and reset switch (reset unit) RS that are provided in parallel between the first input terminal and the output terminal. The sensing signal line 125 is connected to the first input terminal, and a reference potential REF is supplied to the second terminal. The sampling switch SW is arranged between the output terminal of the differential amplifier DA (amplification circuit AMP) and the holding capacitor HC. VA is the potential of the second electrode 151 of the sensing pixel 121, and VB is the potential of the output terminal of the differential amplifier DA (amplification circuit AMP). The "driving signal" in FIGS. 8 and 9 is a signal that is applied to the driving line 124.

During irradiation of radiation (period T2 in FIG. 4), the potential of the second electrodes 151 of the imaging pixels 101 varies. Accompanying this, the potential of the sensing signal lines 125 changes due to crosstalk via the parasitic capacitances between the second electrodes 151 and the sensing signal lines 125. Accordingly, as illustrated in FIG. 8 (comparative example), the potential VB of the output terminal of the differential amplifier DA (amplification circuit AMP) also varies. In FIG. 8, the "crosstalk component" indicates a change in VB corresponding to a change in the potential of the sensing signal line 125 due to crosstalk. Also, the "radiation component" indicates a change in VB corresponding to a change in the potential of the sensing signal line 125 (i.e., charges accumulated in the second conversion elements 122) caused by the second switch 123 being turned on. The "cross talk component" and the "radiation component" are included in the signal accumulated in the holding capacitor HC due to the sampling signal SH being switched to the high level so as to cause the sampling switch SW to turn on.

Hereinafter, an operation for reducing the influence of crosstalk will be described with reference to FIG. 9. First, the reset signal ΦR is switched to the high level at time t0, and the reset switch RS is turned on. Accordingly, VB is reset to the reference potential REF. VB starts to change due to crosstalk at the instant (time t1) that the reset signal ΦR is switched to the low level and the reset switch RS turns off.

Next, sampling is performed on the holding capacitor HC due to the sampling signal SH being switched from the low level to the high level and being furthermore switched from the high level to the low level (until time t2). Accordingly, a signal S1 that corresponds to the crosstalk component is held in the holding capacitor HC. The signal S1 is output via the multiplexer 144 and the AD converter 146.

Next, the reset signal ΦR is switched to the high level at time t3, and the reset switch RS is turned on. Accordingly, VB is reset to the reference potential REF. VB once again starts to change due to crosstalk at the instant (time t4) that the reset signal ΦR is switched to the low level and the reset switch RS turns off.

Next, at times t5 to t6, the second switch 123 is turned on due to the potential of the driving line 124 being switched to the high level. At this time, VB changes according to the amount of charge accumulated in the second conversion element 122. Also, irradiation continues even in a state in which the second switch 123 is turned on, and therefore the potential VB continues to change due to crosstalk.

Next, sampling is performed on the holding capacitor HC due to the sampling signal SH being switched from the low level to the high level and being furthermore switched from the high level to the low level (until time t7). Accordingly, a signal S2 that corresponds to the crosstalk component and the radiation component is held in the holding capacitor HC. The signal S2 is output via the multiplexer 144 and the AD converter 146.

By causing the reset switch RS to turn on in the period from time t3 to time t4, the potential of the sensing signal line 125 is reset to the reference potential REF, and thereby the crosstalk component in the signal S1 and the crosstalk component in the signal S2 become extremely close in value. Accordingly, the signal processing unit 224 calculates the difference between the signal S2 and the signal S1, whereby it is possible to detect the net radiation component (irradiation amount of radiation), or more specifically, to reduce the crosstalk component. Here, by making TT1 and TT2 in FIG. 9 equal, it is possible to reduce the difference between the crosstalk component in the signal S1 and the crosstalk component in the signal S2.

Here, the signal S1 is a signal that appears in the sensing signal line 125 in a state in which the second switch 123 is not caused to turn on after the potential of the sensing signal line 125 is reset to the reference potential REF. The signal S2 is a signal that appears in the sensing signal line 125 due to the second switch 123 being caused to turn on after the potential of the sensing signal line 125 is reset to the reference potential REF.

Period P, during which the readout unit 140 reads out the signal that appears in the sensing signal line 125, includes first period P1 and second period P2. First period P1 includes an operation in which the potential of the sensing signal line 125 is reset by the reset switch (reset unit) RS (t0 to t1), and thereafter, an operation in which the signal that appears in the sensing signal line 125 in a state in which the second switch 123 is not turned on is read out. Second period P2 includes an operation in which the potential of the sensing signal line 125 is reset by the reset switch RS (t3 to t4), and thereafter, an operation in which the signal that appears in the sensing signal line 125 due to the second switch 123 being turned on is read out.

By removing the crosstalk component as described above, it is possible to sense the irradiation amount of the radiation at a high accuracy. In particular, in sensing the start of irradiation of radiation, sensing the integrated irradiation amount of the radiation (radiation dose), and the like, the signal value is small due to the fact that the signal is read out in a short time. For this reason, removing the crosstalk component is of great significance.

In the example shown in FIG. 9, in order to sample the signal S1 and the signal S2, the reset switch RS is turned on in the period from t0 to t1 and in the period from t3 to t4. Here, KTC noise that is determined at the instant that the reset switch RS is turned off cannot be removed by calculating the difference between signal S1 and signal S2. However, by providing a sensing signal line 125 that is different from the column signal line 106, it is possible to reduce the parasitic capacitance of the sensing signal line 125, and therefore the KTC noise can be reduced.

Figure 10:
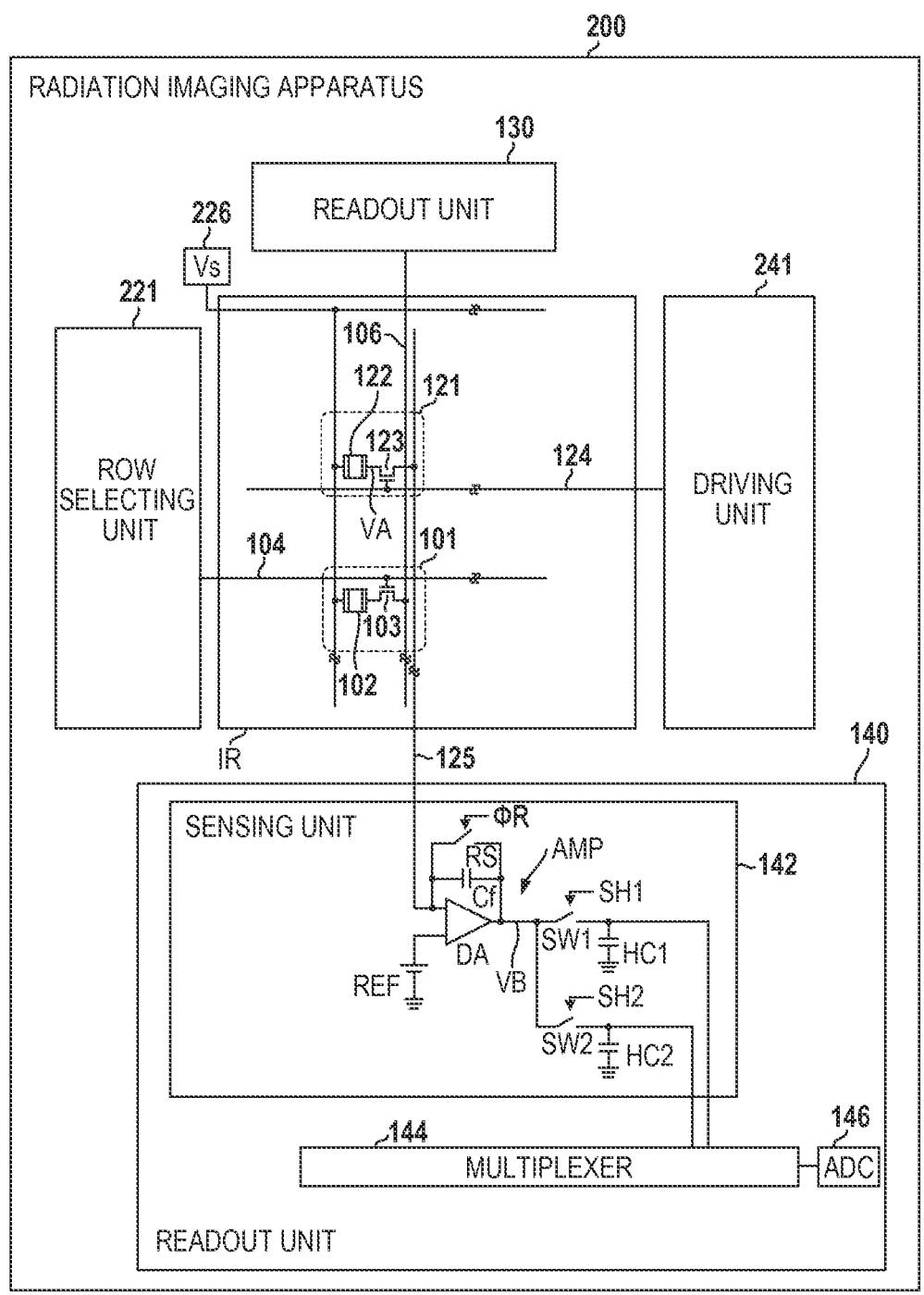
FIG. 10 is a diagram showing a configuration of the radiation imaging apparatus according to a second embodiment of the present invention.
Figure 11:
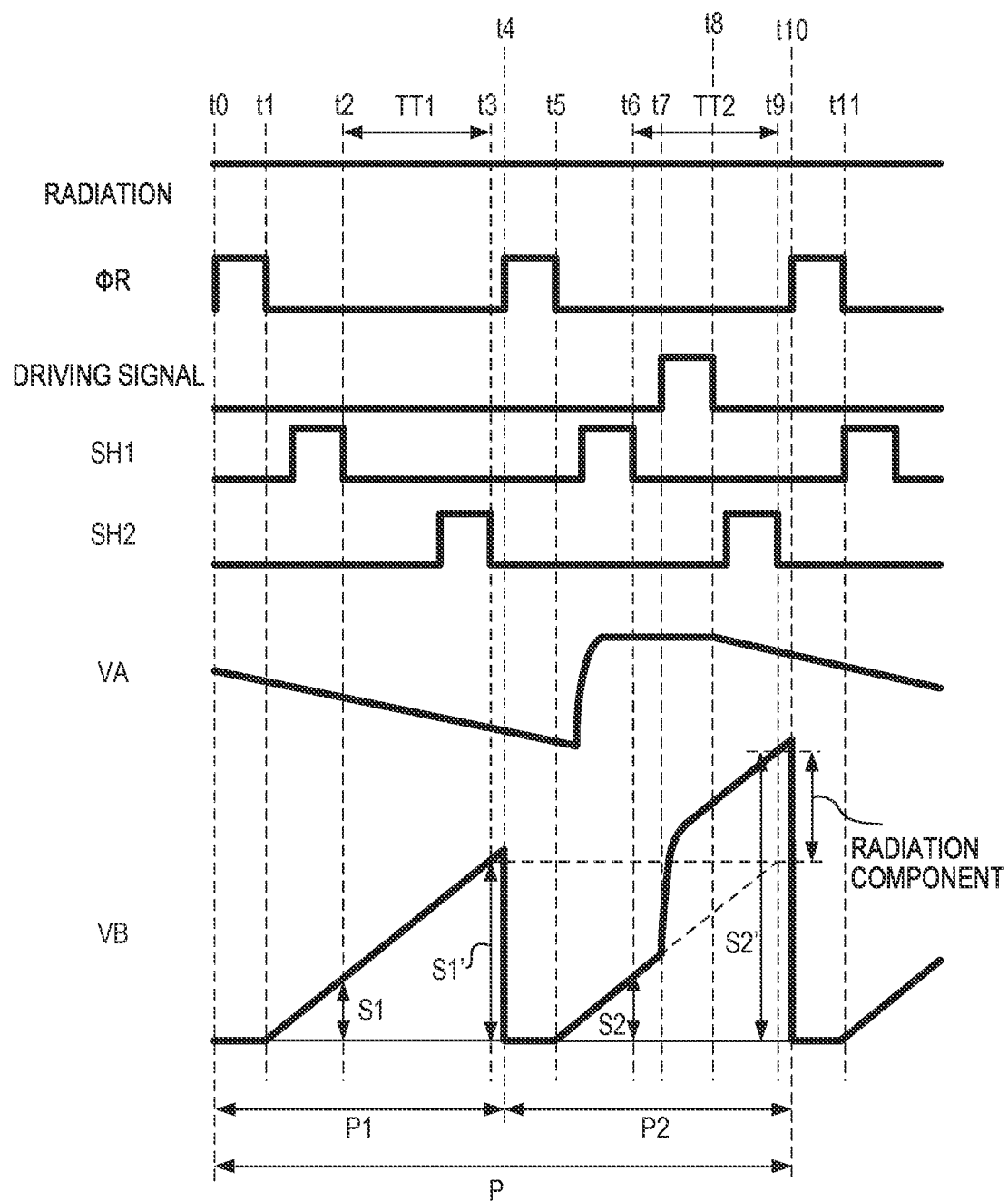
FIG. 11 is a diagram showing operations performed by the radiation imaging apparatus according to the second embodiment of the present invention.

A second embodiment of the present invention will be described next with reference to FIGS. 10 and 11. The second embodiment provides another specific example of the configuration and operations of the readout unit 140. FIG. 10 shows a configuration example of the readout unit 140. FIG. 11 shows an example of operations performed by the readout unit 140 according to the second embodiment. Items not mentioned in the second embodiment may be as described in the first embodiment.

In the second embodiment, the sensing unit 142 includes a first sampling switch SW1, a second sampling switch SW2, a first holding capacitor HC1, and a second holding capacitor HC2, in addition to the amplification circuit AMP.

First, the reset signal ΦR is switched to the high level at time t0, and the reset switch RS is turned on. Accordingly, VB is reset to the reference potential REF. VB starts to change due to crosstalk at the instant (time t1) that the reset signal ΦR is switched to the low level and the reset switch RS turns off.

Next, sampling is performed on the first holding capacitor HC1 due to a first sampling signal SH1 being switched from the low level to the high level and being furthermore switched from the high level to the low level (until time t2). Accordingly, a signal S1 that corresponds to the crosstalk component at time t2 is held in the first holding capacitor HC1.

Next, sampling is performed on the second holding capacitor HC2 due to a second sampling signal SH2 being switched from the low level to the high level and being furthermore switched from the high level to the low level (until time t3). Accordingly, a signal S1' that corresponds to the crosstalk component at time t3 is held in the second holding capacitor HC2. The signals S1 and S1' are output via the multiplexer 144 and the AD converter 146. A difference S1" between the signal S1' and the signal S1 corresponds to the crosstalk component in period TT1. Also, the difference S1" is a difference resulting from two instances of sampling that each occur after the reset switch RS is turned off, and therefore KTC noise is removed.

Next, the reset signal ΦR is switched to the high level at time t4, and the reset switch RS is turned on. Accordingly, VB is reset to the reference potential REF. VB once again starts to change due to crosstalk at the instant (time t5) that the reset signal ΦR is switched to the low level and the reset switch RS turns off.

Next, sampling is performed on the first holding capacitor HC1 due to the first sampling signal SH1 being switched from the low level to the high level and being furthermore switched from the high level to the low level (until time t6). Accordingly, a signal S2 that corresponds to the crosstalk component at time t6 is held in the first holding capacitor HC1.

Next, in the period from t7 to t8, the second switch 123 is turned on due to the potential of the driving line 124 being switched to the high level. At this time, VB changes according to the amount of charge accumulated in the second conversion element 122. Also, irradiation continues even in a state in which the second switch 123 is turned on, and therefore the potential VB continues to change due to crosstalk.

Next, sampling is performed on the second holding capacitor HC2 due to the second sampling signal SH2 being switched from the low level to the high level and being furthermore switched from the high level to the low level (until time t9). Accordingly, a signal S2' that corresponds to the crosstalk component at time t9 is held in the second holding capacitor HC2. The signals S2 and S2' are output via the multiplexer 144 and the AD converter 146. A difference S2" between the signal S2' and the signal S2 corresponds to the crosstalk component and the radiation component in period TT2. Also, the difference S2" is a difference resulting from two instances of sampling that each occur after the reset switch RS is turned off, and therefore KTC noise is removed.

By causing the reset switch RS to turn on in the period from time t4 to time t5, the potential of the sensing signal line 125 is reset to the reference potential REF, and thereby the crosstalk component in the difference S1" and the crosstalk component in the difference S2" become extremely close in value. Accordingly, the signal processing unit 224 calculates the difference between the difference S2" and the difference S1", whereby it is possible to detect the net radiation component (irradiation amount of radiation), or more specifically, to reduce the crosstalk component. Also, the differences S1" and S2" do not include the KTC noise, and therefore the difference between the difference S2" and the difference S1" also does not include the KTC noise. Here, by making TT1 and TT2 in FIG. 11 equal, it is possible to reduce the difference between the crosstalk component in the difference S1" and the crosstalk component in the difference S2".

Here, the difference S1" is the amount of change in the signal that appears in the sensing signal line 125 in a state in which the second switch 123 is not caused to turn on after the potential of the sensing signal line 125 is reset to the reference potential REF. The difference S2" is the amount of change in the signal that appears in the sensing signal line 125 when the second switch 123 is changed from the off state to the on state after the potential of the sensing signal line 125 is reset to the reference potential REF.

Period P, during which the readout unit 140 reads out the signal that appears in the sensing signal line 125 includes first period P1 and second period P2. First period P1 includes an operation in which the potential of the sensing signal line 125 is reset by the reset switch (reset unit) RS (t0 to t1), and thereafter, an operation in which the signal that appears in the sensing signal line 125 in a state in which the second switch 123 is not turned on is read out twice. Second period P2 includes an operation in which the potential of the sensing signal line 125 is reset by the reset switch RS (t3 to t4), and thereafter, an operation in which the signal that appears in the sensing signal line 125 in a state in which the second switch 123 is not turned on is read out. Second period P2 furthermore includes an operation in which the signal that appears in the sensing signal line 125 due to the second switch 123 being turned on is read out. VA is the potential of the second electrode 151 of the imaging pixel 101, and VB is the potential of the output terminal of the differential amplifier DA (amplification circuit AMP).

Figure 12:
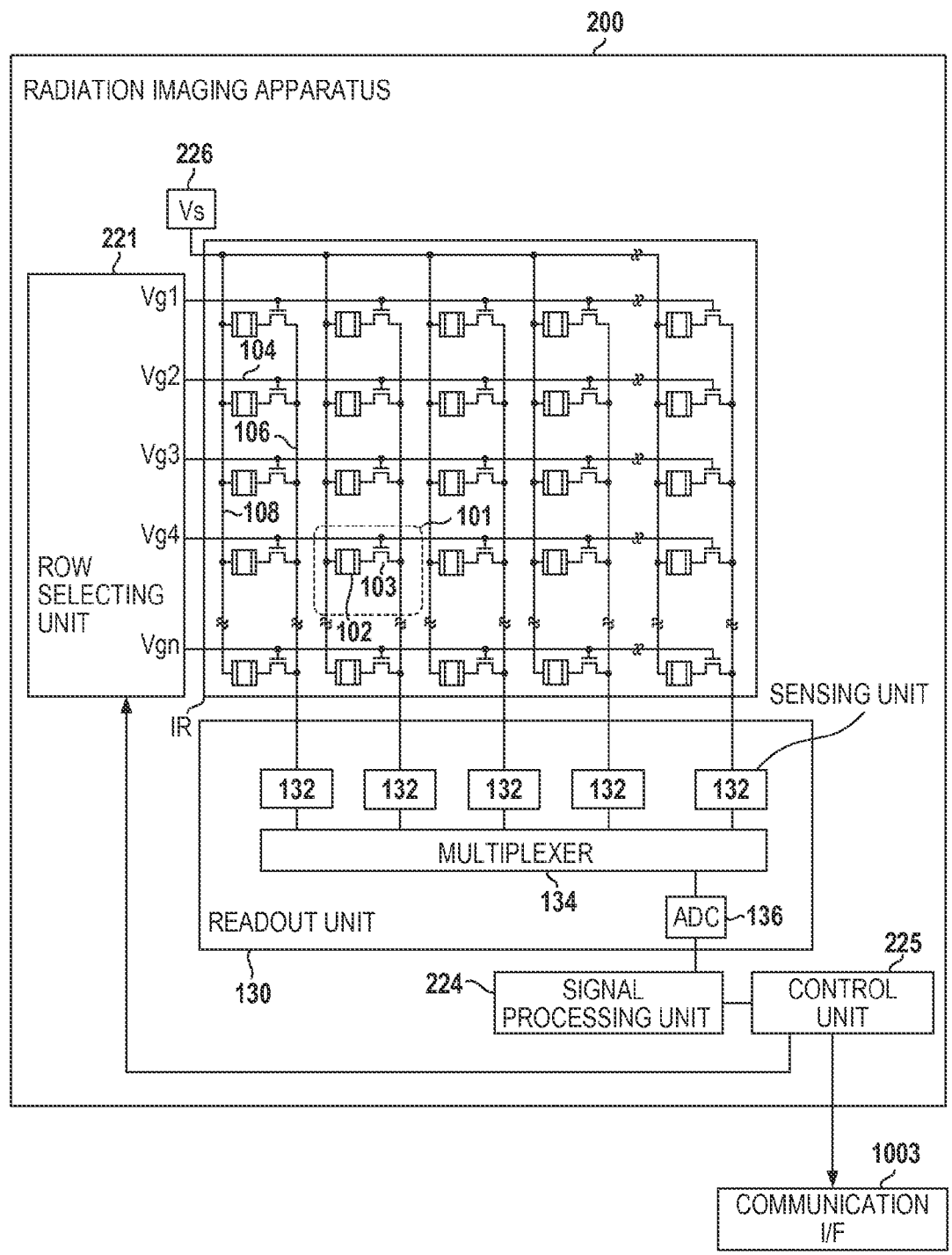
FIG. 12 is a diagram showing a configuration of the radiation imaging apparatus according to a third embodiment of the present invention.
Figure 13:
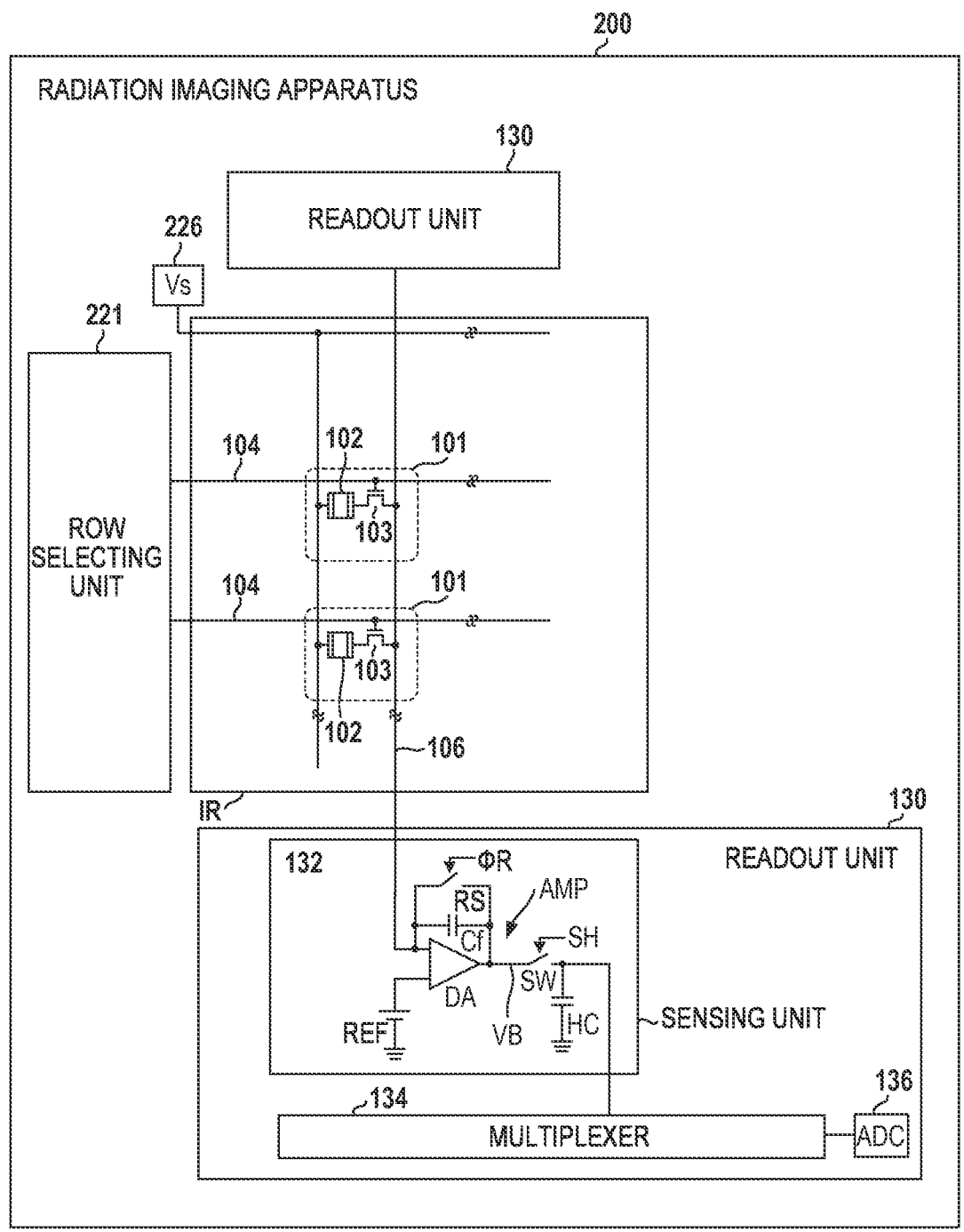
FIG. 13 is a diagram showing a configuration of the radiation imaging apparatus according to the third embodiment of the present invention.

FIG. 12 shows a configuration of the radiation imaging apparatus 200 according to a third embodiment of the present invention. FIG. 13 shows an example of a configuration of the readout unit 130 in the radiation imaging apparatus 200 according to the third embodiment of the present invention. The radiation imaging apparatus 200 according to the third embodiment does not include the sensing pixels 121 and the readout unit 140 that reads out the signals from the sensing pixels 121. Note that the radiation imaging apparatus 200 according to the third embodiment is not characterized by not including the sensing pixels 121 and the readout unit 140, and may include the sensing pixels 121 and the readout unit 140.

The radiation imaging apparatus 200 of the third embodiment reduces the influence of crosstalk that appears in the column signal lines 106 during readout of signals from the imaging pixels 101. Here, in the case where the imaging area IR is irradiated with radiation during readout of a signal from an imaging pixel 101, the potential of the column signal line 106 can change due to crosstalk for the reasons described above. This kind of situation can occur in, for example, the case where the irradiation of radiation has not been stopped at the time when the signal is to be read out from the imaging pixel 101, or in the case of capturing a moving image.

The sensing units 132 of the readout unit 130 can each have a configuration similar to that of the sensing units 142 of the readout unit 140, which was described in the first embodiment. That is to say, the sensing units 132 of the readout unit 130 each include an amplification circuit AMP, a holding capacitor HC, and a sampling switch SW. The amplification circuit AMP includes a differential amplifier DA that has a first input terminal, a second input terminal, and an output terminal, and a feedback capacitor Cf and reset switch (reset unit) RS that are provided in parallel between the first input terminal and the output terminal. The column signal line 106 is connected to the first input terminal, and a reference potential REF is supplied to the second terminal. The sampling switch SW is arranged between the output terminal of the differential amplifier DA (amplification circuit AMP) and the holding capacitor HC.

Hereinafter, operations of the radiation imaging apparatus 200 according to the third embodiment will be described with reference to FIG. 9. In the description of the third embodiment, the "driving signal" in FIG. 9 is a signal that is applied to the driving line 104. First, the reset signal ΦR is switched to the high level at time t0, and the reset switch RS is turned on. Accordingly, VB is reset to the reference potential REF. VB starts to change due to crosstalk at the instant (time t1) that the reset signal ΦR is switched to the low level and the reset switch RS turns off.

Next, sampling is performed on the holding capacitor HC due to the sampling signal SH being switched from the low level to the high level and being furthermore switched from the high level to the low level (until time t2). Accordingly, a signal S1 that corresponds to the crosstalk component is held in the holding capacitor HC. The signal S1 is output via the multiplexer 144 and the AD converter 146.

Next, the reset signal ΦR is switched to the high level at time t3, and the reset switch RS is turned on. Accordingly, VB is reset to the reference potential REF. VB once again starts to change due to crosstalk at the instant (time t4) that the reset signal ΦR is switched to the low level and the reset switch RS turns off.

Next, at times t5 to t6, the first switch 103 is turned on due to the potential of the driving line 104 being switched to the high level. At this time, VB changes according to the amount of charge accumulated in the first conversion element 102. Also, irradiation continues even in a state in which the first switch 103 is turned on, and therefore the potential VB continues to change due to crosstalk.

Next, sampling is performed on the holding capacitor HC due to the sampling signal SH being switched from the low level to the high level and being furthermore switched from the high level to the low level (until time t7). Accordingly, a signal S2 that corresponds to the crosstalk component and the radiation component is held in the holding capacitor HC. The signal S2 is output via the multiplexer 134 and the AD converter 136.

By causing the reset switch RS to turn on in the period from time t3 to time t4, the potential of the column signal line 106 is reset to the reference potential REF, and thereby the crosstalk component in the signal S1 and the crosstalk component in the signal S2 become extremely close in value. Accordingly, the signal processing unit 224 calculates the difference between the signal S2 and the signal S1, whereby it is possible to detect the net radiation component (irradiation amount of radiation), or more specifically, to reduce the crosstalk component. Here, by making TT1 and TT2 in FIG. 9 equal, it is possible to reduce the difference between the crosstalk component in the signal S1 and the crosstalk component in the signal S2.

Here, the signal S1 is a signal that appears in the column signal line 106 in a state in which the second switch 123 is not caused to turn on after the potential of the column signal line 106 is reset to the reference potential REF. The signal S2 is a signal that appears in the column signal line 106 due to the second switch 123 being caused to turn on after the potential of the column signal line 106 is reset to the reference potential REF.

Period P, during which the readout unit 130 reads out the signal that appears in the column signal line 106, includes first period P1 and second period P2. First period P1 includes an operation in which the potential of the column signal line 106 is reset by the reset switch (reset unit) RS (t0 to t1), and thereafter, an operation in which the signal that appears in the column signal line 106 in a state in which the second switch 123 is not turned on is read out. Second period P2 includes an operation in which the potential of the column signal line 106 is reset by the reset switch RS (t3 to t4), and thereafter, an operation in which the signal that appears in the column signal line 106 due to the second switch 123 being turned on is read out.

Figure 14:
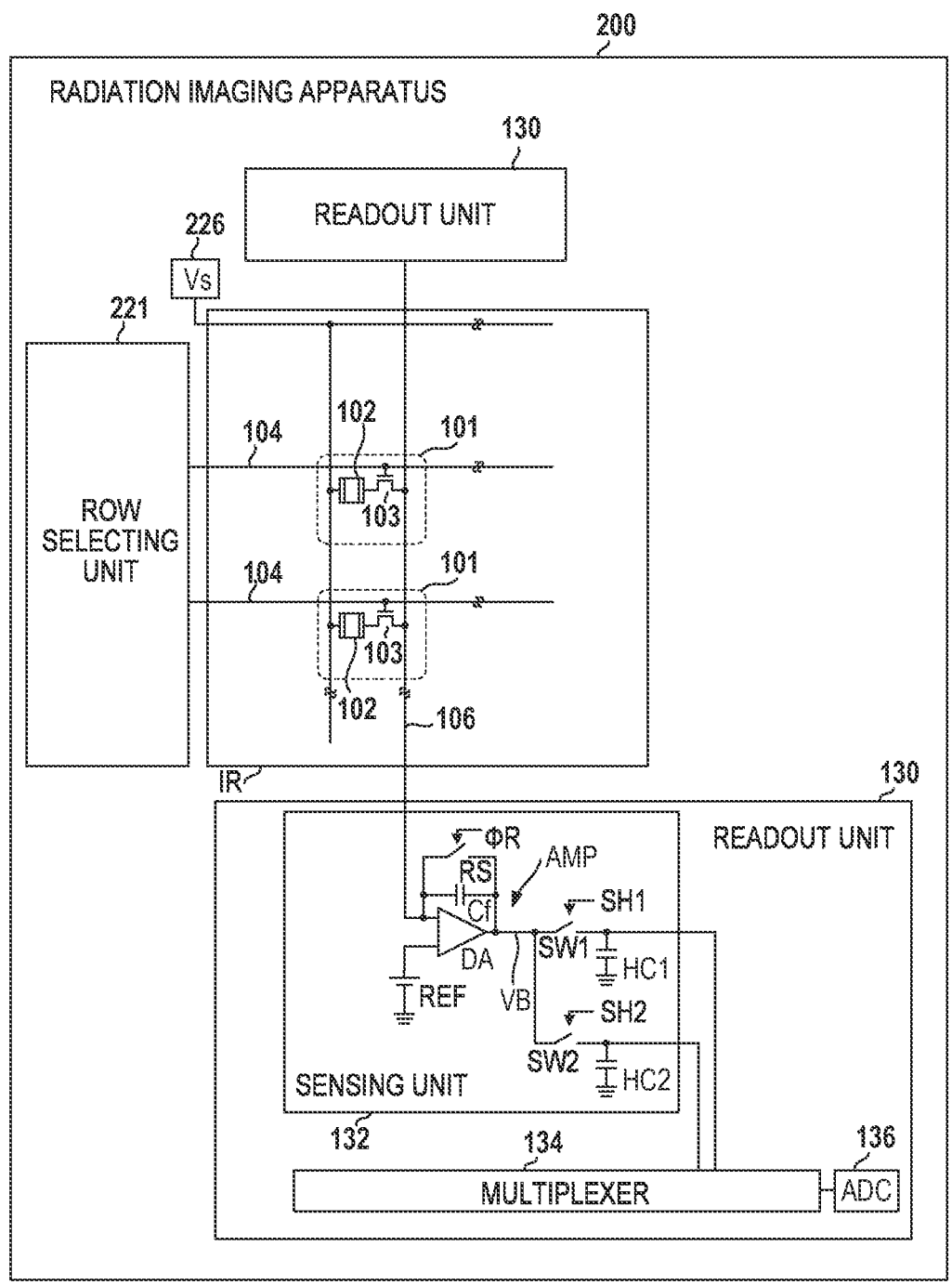
FIG. 14 is a diagram showing a configuration of the radiation imaging apparatus according to a fourth embodiment of the present invention.

FIG. 14 shows an example of a configuration of the readout unit 130 in the radiation imaging apparatus 200 according to a fourth embodiment of the present invention. Items not mentioned in the fourth embodiment may be as described in the third embodiment. The radiation imaging apparatus 200 of the fourth embodiment reduces the influence of crosstalk that appears in the column signal lines 106 during readout of signals from the imaging pixels 101.

The sensing units 132 of the readout unit 130 according to the fourth embodiment can each have a configuration similar to that of the sensing unit 142 of the readout unit 140 described in the second embodiment. In other words, the sensing units 132 of the readout unit 130 each have a first sampling switch SW1, a second sampling switch SW2, a first holding capacitor HC1, and a second holding capacitor HC2, in addition to the amplification circuit AMP.

Hereinafter, operations of the radiation imaging apparatus 200 according to the fourth embodiment will be described with reference to FIG. 11. In the description of the fourth embodiment, the "driving signal" in FIG. 11 is a signal that is applied to the driving line 104. First, the reset signal ΦR is switched to the high level at time t0, and the reset switch RS is turned on. Accordingly, VB is reset to the reference potential REF. VB starts to change due to crosstalk at the instant (time t1) that the reset signal ΦR is switched to the low level and the reset switch RS turns off.

Next, sampling is performed on the first holding capacitor HC1 due to a first sampling signal SH1 being switched from the low level to the high level and being furthermore switched from the high level to the low level (until time t2). Accordingly, a signal S1 that corresponds to the crosstalk component at time t2 is held in the first holding capacitor HC1.

Next, sampling is performed on the second holding capacitor HC2 due to a second sampling signal SH2 being switched from the low level to the high level and being furthermore switched from the high level to the low level (until time t3). Accordingly, a signal S1' that corresponds to the crosstalk component at time t3 is held in the second holding capacitor HC2. The signals S1 and S1' are output via the multiplexer 144 and the AD converter 146. A difference S1" between the signal S1' and the signal S1 corresponds to the crosstalk component in period TT1. Also, the difference S1" is a difference resulting from two instances of sampling that each occur after the reset switch RS is turned off, and therefore KTC noise is removed.

Next, the reset signal ΦR is switched to the high level at time t4, and the reset switch RS is turned on. Accordingly, VB is reset to the reference potential REF. VB once again starts to change due to crosstalk at the instant (time t5) that the reset signal ΦR is switched to the low level and the reset switch RS turns off.

Next, sampling is performed on the first holding capacitor HC1 due to the first sampling signal SH1 being switched from the low level to the high level and being furthermore switched from the high level to the low level (until time t6). Accordingly, a signal S2 that corresponds to the crosstalk component at time t6 is held in the first holding capacitor HC1.

Next, in the period from time t7 to time t8, the first switch 103 is turned on due to the potential of the driving line 104 being switched to the high level. At this time, VB changes according to the amount of charge accumulated in the first conversion element 102. Also, irradiation continues even in a state in which the first switch 103 is turned on, and therefore the potential VB continues to change due to crosstalk.

Next, sampling is performed on the second holding capacitor HC2 due to the second sampling signal SH2 being switched from the low level to the high level and being furthermore switched from the high level to the low level (until time t9). Accordingly, a signal S2' that corresponds to the crosstalk component at time t9 is held in the second holding capacitor HC2. The signals S2 and S2' are output via the multiplexer 134 and the AD converter 136. A difference S2" between the signal S2' and the signal S2 corresponds to the crosstalk component and the radiation component in period TT2. Also, the difference S2" is a difference resulting from two instances of sampling that each occur after the reset switch RS is turned off, and therefore KTC noise is removed.

By causing the reset switch RS to turn on in the period from time t4 to time t5, the potential of the column signal line 106 is reset to the reference potential REF, and thereby the crosstalk component in the difference S1" and the crosstalk component in the difference S2" become extremely close in value. Accordingly, the signal processing unit 224 calculates the difference between the difference S2" and the difference S1", whereby it is possible to detect the net radiation component (irradiation amount of radiation), or more specifically, to reduce the crosstalk component. Also, the differences S1" and S2" do not include the KTC noise, and therefore the difference between the difference S2" and the difference S1" also does not include the KTC noise. Here, by making TT1 and TT2 in FIG. 11 equal, it is possible to reduce the difference between the crosstalk component in the difference S1" and the crosstalk component in the difference S2".

Here, the difference S1" is the amount of change in a signal that appears in the column signal line 106 in a state in which the first switch 103 is not caused to turn on after the potential of the column signal line 106 is reset to the reference potential REF. The difference S2" is the amount of change in a signal that appears in the column signal line 106 when the second switch 123 is changed from the off state to the on state after the potential of the column signal line 106 is reset to the reference potential REF.

Period P, during which the readout unit 130 reads out the signal that appears in the column signal line 106, includes first period P1 and second period P2. First period P1 includes an operation in which the potential of the column signal line 106 is reset by the reset switch (reset unit) RS (t0 to t1), and thereafter, an operation in which the signal that appears in the column signal line 106 in a state in which the first switch 103 is not turned on is read out twice. Second period P2 includes an operation in which the potential of the column signal line 106 is reset by the reset switch RS (t3 to t4), and thereafter, an operation in which the signal that appears in the column signal line 106 in a state in which the first switch 103 is not turned on is read out. Second period P2 furthermore includes an operation in which the signal that appears in the column signal line 106 due to the first switch 103 being turned on is read out. VA is the potential of the second electrode 151 of the imaging pixel 101, and VB is the potential of the output terminal of the differential amplifier DA (amplification circuit AMP).

Figure 15:
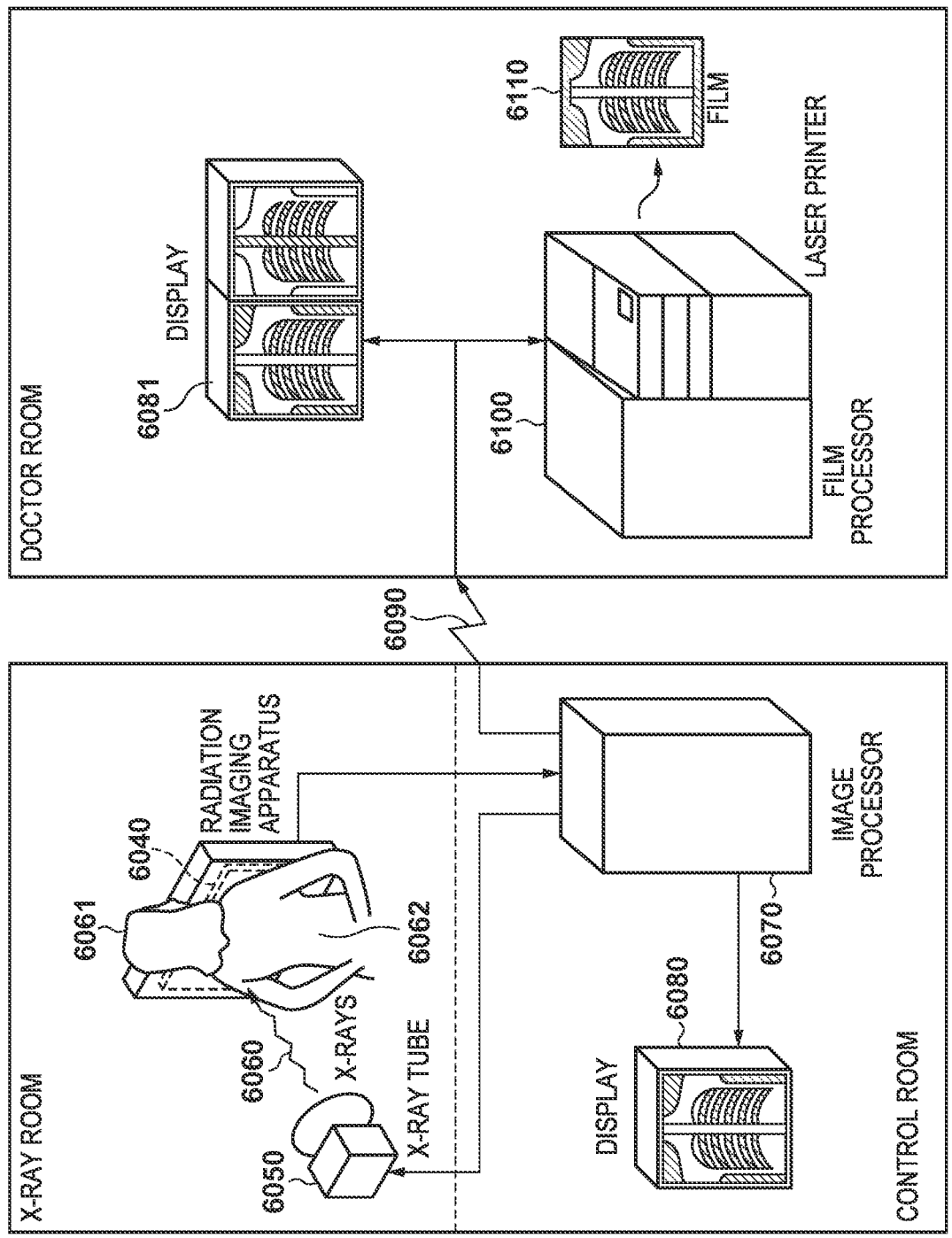
FIG. 15 is a diagram showing an example of a configuration of a radiation imaging system.

Hereinafter, with reference to FIG. 15, an example will be described in which the radiation imaging apparatus 200 is applied to a radiation imaging system. X-rays 6060 emitted by an X-ray tube 6050, which is a radiation source, pass through a chest portion 6062 of a patient or examination subject 6061 and are incident on a radiation imaging apparatus 6040, which is represented by the above-described radiation imaging apparatus 200. The received X-rays include information about the interior of the body of the examination subject 6061. The scintillator 216 emits light in correspondence with the incident X-rays, the light is photoelectrically converted using photoelectric conversion elements, and thereby electrical information is obtained. This information is digitally converted, is subjected to image processing by an image processor 6070, which is a signal processing means, and can be observed using a display 6080, which is a display means in a control room.

Also, the information can be transferred to a remote location by a transfer processing means such as a telephone line 6090, can be displayed on a display 6081, which is a displaying means, in a doctor room or the like at another location, or stored in a storing means such as an optical disk, and a doctor at the remote location can also perform diagnosis. The information can also be recorded on film 6110, which is a recording medium, by a film processor 6100, which is a recording means.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-094876, filed May 1, 2014, which is hereby incorporated by reference herein in its entirety.

What is claimed is:

1. A radiation imaging apparatus, comprising:
   a pixel including a conversion element configured to convert radiation into an electric signal, and a switch configured to connect the conversion element to a signal line;
   a readout unit configured to read out a signal that appears in the signal line;
   a reset unit configured to reset a potential of the signal line; and
   a signal processing unit,
   wherein a period during which the readout unit reads out a signal that appears in the signal line includes
      a first period during which the potential of the signal line is reset by the reset unit, and thereafter, a signal that appears in the signal line in a state in which the switch is not turned on is read out, and
      a second period during which the potential of the signal line is reset by the reset unit, and thereafter, a signal that appears in the signal line due to the switch being turned on is read out, and
   wherein the signal processing unit calculates a difference between the signal read out by the readout unit in the second period and the signal read out by the readout unit in the first period.

2. The radiation imaging apparatus according to claim 1, wherein
   the pixel is a pixel for monitoring irradiation of radiation,
   in addition to the pixel, the radiation imaging apparatus includes a plurality of imaging pixels for capturing a radiation image, and
   the pixel for monitoring irradiation of radiation is arranged in the same column as a portion of the plurality of imaging pixels.

3. The radiation imaging apparatus according to claim 2, wherein signals of the plurality of imaging pixels are read out via a signal line that is different from the signal line.

4. The radiation imaging apparatus according to claim 1, wherein
   the pixel is a pixel for capturing a radiation image, and
   a moving image is formed using a signal read out from the pixel by the readout unit.

5. The radiation imaging apparatus according to claim 1, wherein the readout unit includes a differential amplifier that has a first input terminal to which an electric signal is applied via the signal line, a second input terminal to which a reference potential is applied, and an output terminal, and the reset unit includes a switch configured to connect the first input terminal and the output terminal.

6. A radiation imaging system, comprising:
   a radiation source configured to generate radiation; and
   the radiation imaging apparatus according to claim 1,
   wherein when an integrated value of the difference between the signal read out by the readout unit in the second period and the signal read out by the readout unit in the first period reaches a predetermined value, an exposure stop signal is sent to the radiation source, and the radiation source stops radiating radiation in response to the exposure stop signal.

7. A radiation imaging apparatus, comprising:

a pixel including a conversion element configured to convert radiation into an electric signal, and a switch configured to connect the conversion element to a signal line;

a readout unit configured to read out a signal that appears in the signal line;

a reset unit configured to reset a potential of the signal line; and a signal processing unit, wherein a period during which the readout unit reads out a signal that appears in the signal line includes:

a first period during which the potential of the signal line is reset by the reset unit, and thereafter, a signal that appears in the signal line in a state in which the switch is not turned on is read out twice, and a second period during which the potential of the signal line is reset by the reset unit, a signal that appears in the signal line in a state in which the switch is not turned on is read out by the readout unit, and thereafter, a signal that appears in the signal line due to the switch being turned on is read out, and wherein the signal processing unit calculates a difference between a first difference and a second difference, the first difference being a difference between the signal that appears in the signal line due to the switch being turned on in the second period and the signal that appears in the signal line in a state in which the switch is not turned on in the second period, and the second difference being a difference between the signals read out twice in the first period.

8. The radiation imaging apparatus according to claim 7, wherein the pixel is a pixel for monitoring irradiation of radiation, in addition to the pixel, the radiation imaging apparatus includes a plurality of imaging pixels for capturing a radiation image, and the pixel for monitoring irradiation of radiation is arranged in the same column as a portion of the plurality of imaging pixels.

9. The radiation imaging apparatus according to claim 8, wherein signals of the plurality of imaging pixels are read out via a signal line that is different from the signal line.

10. The radiation imaging apparatus according to claim 7, wherein the pixel is a pixel for capturing a radiation image, and a moving image is formed using a signal read out from the pixel by the readout unit.

11. The radiation imaging apparatus according to claim 7, wherein the readout unit includes a differential amplifier that has a first input terminal to which an electric signal is applied via the signal line, a second input terminal to which a reference potential is applied, and an output terminal, and the reset unit includes a switch configured to connect the first input terminal and the output terminal.

12. A radiation imaging system, comprising:

a radiation source configured to generate radiation; and the radiation imaging apparatus according to claim 7, wherein when an integrated value of the difference between the first difference and the second difference reaches a predetermined value, an exposure stop signal is sent to the radiation source, and the radiation source stops radiating radiation in response to the exposure stop signal.

13. The radiation imaging apparatus according to claim 1, wherein the readout unit includes the reset unit.

* * * * *